United States Patent
Muller-Spanka et al.

(10) Patent No.: US 9,808,565 B2
(45) Date of Patent: Nov. 7, 2017

(54) CARDIOPULMONARY APPARATUS AND METHODS FOR USE DURING PCI AND CABG

(71) Applicant: ZOLL LifeBridge GmbH, Ampfing (DE)

(72) Inventors: Gerhard Muller-Spanka, Emmering (DE); Hans Reinhard-Zerkowski, Riehen (CH)

(73) Assignee: ZOLL LifeBridge GmbH, Ampfing (DE)

(*) Notice: Subject to any disclaimer, the term of this patent is extended or adjusted under 35 U.S.C. 154(b) by 0 days.

(21) Appl. No.: 14/275,634

(22) Filed: May 12, 2014

(65) Prior Publication Data

US 2015/0073335 A1 Mar. 12, 2015

Related U.S. Application Data

(63) Continuation of application No. 12/962,626, filed on Dec. 7, 2010, now Pat. No. 8,721,579.

(51) Int. Cl.
*A61M 1/34* (2006.01)
*A61M 1/36* (2006.01)
(Continued)

(52) U.S. Cl.
CPC ............ *A61M 1/34* (2013.01); *A61M 1/1698* (2013.01); *A61M 1/32* (2013.01); *A61M 1/3612* (2014.02);
(Continued)

(58) Field of Classification Search
CPC ........ A61M 1/1698; A61M 1/32; A61M 1/34; A61M 1/3612; A61M 1/3621; A61M 1/3626; A61M 1/3627; A61M 1/3643; A61M 1/3666; A61M 1/3693; A61M 2016/0015; A61M 2205/505;
(Continued)

(56) References Cited

U.S. PATENT DOCUMENTS

| 3,567,028 A | 3/1971 | Nose |
|---|---|---|
| 3,744,762 A | 7/1973 | Schlicht |

(Continued)

FOREIGN PATENT DOCUMENTS

| DE | 3834952 A1 | 4/1989 |
|---|---|---|
| DE | 19534502 A1 | 3/1997 |

(Continued)

OTHER PUBLICATIONS

Japanese Patent Office, Examiner's Report mailed Dec. 22, 2009 in Japanese Patent Application No. JP2005-335622, 4 pages.

(Continued)

*Primary Examiner* — Adam Marcetich
(74) *Attorney, Agent, or Firm* — Robert D. Buyan; Stout, Uxa & Buyan, LLP

(57) ABSTRACT

Apparatus and methods for providing extracorporeal blood circulation and oxygenation control include multi-stage deairing of blood to provide automated cardiopulmonary replacement to sustain patient life during a medical procedure such as cardiopulonary bypass graft surgery, keyhole cardiopulmonary bypass graft surgery, percutaneous angioplasty, percutaneous stent placement, and percutaneous atherectomy.

7 Claims, 15 Drawing Sheets

(51) Int. Cl.

| | | |
|---|---|---|
| *A61M 39/28* | (2006.01) | |
| *A61M 39/22* | (2006.01) | |
| *A61M 1/16* | (2006.01) | |
| *A61M 1/32* | (2006.01) | |
| *F04B 43/12* | (2006.01) | |
| *A61M 16/00* | (2006.01) | |
| *F16K 31/00* | (2006.01) | |
| *F16K 35/00* | (2006.01) | |

(52) U.S. Cl.
CPC ........ *A61M 1/3621* (2013.01); *A61M 1/3626* (2013.01); *A61M 1/3627* (2013.01); *A61M 1/3643* (2013.01); *A61M 1/3666* (2013.01); *A61M 1/3693* (2013.01); *A61M 39/281* (2013.01); *F04B 43/12* (2013.01); *A61M 2016/0015* (2013.01); *A61M 2205/505* (2013.01); *A61M 2209/08* (2013.01); *F16K 31/00* (2013.01); *F16K 35/00* (2013.01)

(58) Field of Classification Search
CPC . A61M 2209/08; A61M 39/281; F04B 43/12; F16K 31/00; F16K 35/00
See application file for complete search history.

(56) References Cited

U.S. PATENT DOCUMENTS

| | | | |
|---|---|---|---|
| 4,466,804 A | 8/1984 | Hino | |
| 4,562,984 A | 1/1986 | Sherlock et al. | |
| 4,612,170 A | 9/1986 | Luther et al. | |
| 4,620,965 A | 11/1986 | Fukusawa et al. | |
| 4,876,066 A | 10/1989 | Bringham et al. | |
| 4,925,152 A | 5/1990 | Huber | |
| 5,084,244 A | 1/1992 | Muramoto | |
| RE33,932 E | 5/1992 | Fukasawa et al. | |
| 5,188,604 A | 2/1993 | Orth | |
| 5,232,437 A | 8/1993 | Lysaght et al. | |
| 5,308,320 A * | 5/1994 | Safar | A61M 1/3621 604/113 |
| 5,350,357 A | 9/1994 | Kamen et al. | |
| 5,391,142 A | 2/1995 | Sites et al. | |
| 5,820,579 A | 10/1998 | Plotkin | |
| 5,823,986 A | 10/1998 | Peterson | |
| 5,950,670 A | 9/1999 | Flaim | |
| 6,039,078 A | 3/2000 | Tamari | |
| 6,071,257 A | 6/2000 | Stojanovic | |
| 6,071,258 A | 6/2000 | Dalke et al. | |
| 6,302,860 B1 | 10/2001 | Gremel et al. | |
| 6,503,450 B1 * | 1/2003 | Afzal | A61M 1/101 422/45 |
| 6,579,257 B1 | 6/2003 | Elgas et al. | |
| 6,695,803 B1 | 2/2004 | Robinson et al. | |
| 6,748,815 B2 | 6/2004 | Povey et al. | |
| 7,367,540 B2 | 5/2008 | Brieske | |
| 7,597,546 B2 | 10/2009 | Brieske | |
| 2001/0016725 A1 * | 8/2001 | Valley | A61B 17/00234 604/509 |
| 2002/0026944 A1 * | 3/2002 | Aboul-Hosn | A61F 2/82 128/898 |
| 2002/0031442 A1 | 3/2002 | Knott | |
| 2002/0057989 A1 * | 5/2002 | Afzal | A61M 1/1698 422/45 |
| 2002/0085952 A1 | 7/2002 | Ellingboe et al. | |
| 2003/0163077 A1 * | 8/2003 | Kim | A61M 1/16 604/5.01 |
| 2003/0163078 A1 * | 8/2003 | Fallen | A61M 1/3664 604/6.01 |
| 2005/0004480 A1 * | 1/2005 | Kirchhof | A61M 1/1698 600/504 |
| 2005/0027231 A1 * | 2/2005 | Kirchhof | A61M 1/3621 604/4.01 |
| 2005/0084416 A1 * | 4/2005 | Thomas | A61M 1/3621 422/45 |
| 2005/0090774 A1 * | 4/2005 | Tonelli | A61M 39/281 604/5.01 |
| 2006/0122551 A1 | 6/2006 | Brieske | |
| 2007/0146342 A1 | 6/2007 | Medler et al. | |
| 2008/0027368 A1 * | 1/2008 | Kollar | A61M 1/3621 604/6.14 |
| 2008/0171960 A1 | 7/2008 | Brieske et al. | |
| 2009/0054822 A1 * | 2/2009 | Murakami | A61M 1/3653 604/6.1 |
| 2009/0112049 A1 * | 4/2009 | Ahmed | A61M 1/1037 600/16 |
| 2009/0275875 A1 * | 11/2009 | Liebing | A61M 1/3632 604/6.09 |
| 2009/0312686 A1 * | 12/2009 | Sakamoto | A61M 1/3643 604/6.11 |
| 2010/0121246 A1 * | 5/2010 | Peters | A61M 1/342 604/6.04 |
| 2010/0262063 A1 * | 10/2010 | O'Neill | A61M 1/3664 604/6.11 |

FOREIGN PATENT DOCUMENTS

| | | |
|---|---|---|
| DE | 29719899 U1 | 1/1998 |
| DE | 19702098 A1 | 7/1998 |
| DE | 19905937 C1 | 7/2000 |
| EP | 0171749 A1 | 2/1986 |
| EP | 0223864 A1 | 6/1987 |
| EP | 1661592 A1 | 5/2006 |
| FR | 2368284 A1 | 5/1978 |
| JP | 2002527212 T | 8/2002 |
| JP | 2002536126 T | 10/2002 |
| JP | 2003180824 A | 7/2003 |
| WO | WO95/11709 A2 | 5/1995 |
| WO | WO02/26288 A2 | 4/2002 |
| WO | WO2004/098678 A1 | 11/2004 |

OTHER PUBLICATIONS

United States Patent and Trademark Office, Final Office Action mailed Dec. 8, 2009 in U.S. Appl. No. 11/284,515, 10 pages.
United States Patent and Trademark Office, Office Action mailed May 27, 2009 in U.S. Appl. No. 11/284,515, 13 pages.
European Patent Office, Decision to Grant dated May 6, 2008 in European Patent Application No. EP04027855.8-2310/1661592, 2 pages.
European Patent Office, European Search Report dated Aug. 10, 2007 in European Patent Application No. EP07010455.9-231O, 7 pages.
European Patent Office, Translation of European Search Report dated Apr. 20, 2005 in European Patent Application No. EP04027855.8, 4 pages.
United States Patent and Trademark Office, Office Action mailed Apr. 21, 2010 in U.S. Appl. No. 11/284,515, 11 pages.

* cited by examiner

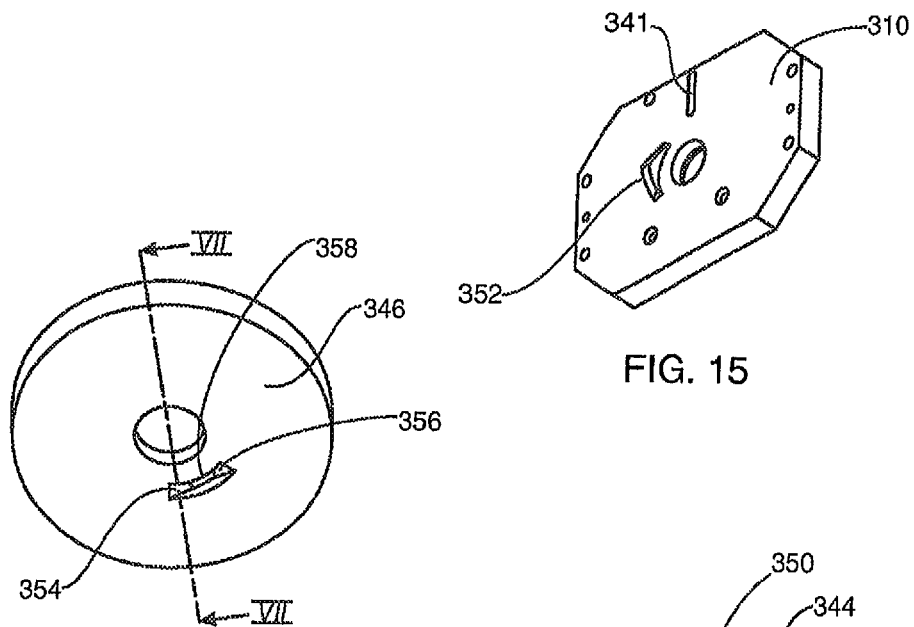
FIG. 15
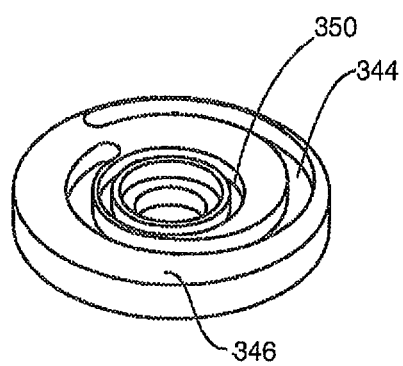
FIG. 16
FIG. 17
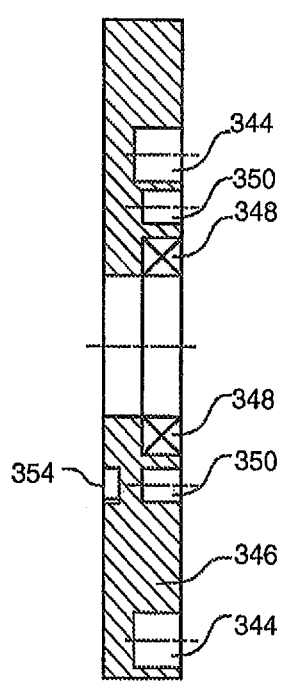
FIG. 18
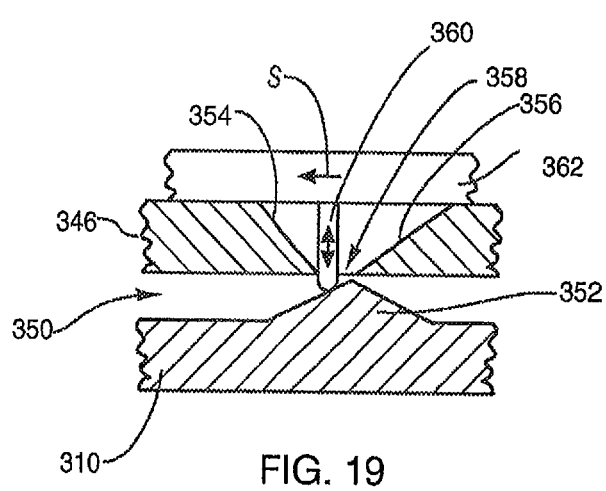
FIG. 19

CARDIOPULMONARY APPARATUS AND METHODS FOR USE DURING PCI AND CABG

RELATED APPLICATIONS

This application is a continuation of U.S. patent application Ser. No. 12/962,626 filed Dec. 7, 2010 and issuing May 13, 2014 as U.S. Pat. No. 8,721,579, the entire disclosure of which is expressly incorporated herein by reference.

This application is also related to U.S. patent application Ser. No. 11/284,515 filed Nov. 22, 2005 entitled Apparatus For Making Extracorporeal Blood Circulation Available; European Patent Application No. EP 04 027 855.8 filed on Nov. 24, 2004 entitled Vorrichtung zur Bereitstellung eines estrakorporalen Blutkreislaufs (Device For Providing An Extracorporeal Blood Circuit) and U.S. patent application Ser. No. 11/554,524 filed Oct. 30, 2006 entitled Apparatus For Making Extracorporeal Blood Circulation Available, the entire disclosure of each such application being expressly incorporated herein by reference.

BACKGROUND OF THE INVENTION

Field of the Invention

The present invention relates to cardiopulmonary apparatus and methods for preserving the life of a patient by providing extracorporeal blood oxygenation and circulation in which a patient's blood is introduced via a venous connection into the extracorporeal blood circuit and is pumped by a blood pump via different blood-conducting components to an arterial connection from where the blood is again pumped into the patient's blood circulation.

The apparatus and methods are useful in a variety of medical procedures including Percutaneous Coronary Intervention (PCI) such as angioplasty and drug-eluting and non-drug-eluting stent placement and Coronary Artery Bypass Graft (CABG) procedures. The apparatus, methods, and systems are necessary for sustaining the life of a patient while the heart is slowed or stopped during PCI or CABG.

Description of Related Art

Time is critical during PCI and CABG procedures. Less time required to perform these procedures generally correlates with a lower risk of complications and mortality. When artificial cardiopulmonary assistance is required, the priming and bringing into operation of a heart-lung machine can be time consuming and requires medical staff specialized in perfusion.

Additionally, during machine priming, a liquid is used to fill the blood-conducting components of the heart-lung machine. The priming liquid must be vented or deaerated prior to connection with the patient's vascular system and initiating heart-lung machine operation in order to eliminate air bubbles, which can cause thrombosis. When such an extracorporeal blood circuit is used, air bubbles may form inside the blood circuit and air present in the blood circuit while putting the extracorporeal blood circuit into operation can enter into the blood. An air bubble entering into the patient's blood circulation can cause a fatal air embolism in the worst case. Air bubble detectors can detect air bubbles in the extracorporeal blood circuit to trigger a visual or acoustic alarm signal so that the blood supply to the patient can be stopped. Subsequently, medical personnel on hand must act as fast as possible to eliminate the problem.

The apparatus and methods of the present invention overcome the aforementioned limitations of prior art heart-lung machines by providing for a compact and portable heart-lung machine that can be primed and ready for operation in less than 10 minutes with little or no human intervention. The present heart-lung machine may be selfcontained and include an internal power supply, and/or may be connected to an external power supply such as an on-board power supply of an emergency land, air, or sea transport vehicle. Furthermore, no perfusion specialist is required for set up or operation and, in some embodiments, the machine may be constructed to meet requirements for regulatory approval for transport and mobile use. The machine may for instance in particular meet requirements of the EN 1789 standard for use in humid environments, water subjection, and pass shake and crash tests involving up to 10 g forces.

The present invention is made possible, in part, by a number of advancements in heart-lung machine technology including a fast-closing clamp, a fast-priming extracorporeal blood oxygenation, deaeration and circulation system, and an air bubble detection system, which are described in co-assigned U.S. application Ser. Nos. 11/284,515 filed Nov. 22, 2005; Ser. No. 11/366,342, now U.S. Pat. No. 7,597,546 filed Mar. 02, 2006; Ser. No. 11/366,914, now U.S. Pat. No. 7,367,540 filed Mar. 2, 2006; and Ser. No. 11/544,524 filed Oct. 30, 2006, which are incorporated by reference herein in their entirety. The apparatus and methods of the invention are also made possible, in part, by a multistage air removal system and various other components and procedures described herein.

BRIEF SUMMARY OF THE INVENTION

In one aspect, the invention is a method for providing extracorporeal blood circulation to a patient by connecting the patient's circulatory system to a heart-lung machine that is configured for rapid filling and priming by a priming fluid as well as rapid and safe transition to an operational mode. The heart-lung machine comprises a base module and a patient module with pivot means at the base module and/or at the patient module to pivot the patient module relative to the base module about a horizontal axis from a filling position into an operating position.

In a second aspect, the invention is a method for providing extracorporeal blood circulation to a patient by connecting the patient's circulatory system to a heart-lung machine that automatically (i.e. without human intervention) detects and eliminates automatically air bubbles in blood conducting components of the machine, redirects the blood flow through the blood circulating components to prevent the bubbles from entering the patient's circulatory system, removes the bubbles from the circulatory system and, once air bubbles are no longer detected, resumes normal operation. This increases safety with a portable device for the provision of an extracorporeal blood circuit such as is described in U.S. patent application Ser. Nos. 11/284,515 and 10/839,126, which are incorporated by reference herein in their entireties.

In a third aspect, the invention is a method for providing extracorporeal blood circulation to a patient by connecting the patient's circulatory system to a heart-lung machine that comprises a fast acting clamp configured to close an arterial line when a bubble is detected in the blood circulating components of the heart-lung machine.

In a fourth aspect, the invention is a method for providing extracorporeal blood circulation to a patient by connecting the patient's circulatory system to a heart-lung machine that comprises a hose roller pump configured to remove air from a blood reservoir in the heart-lung machine.

The heart-lung machine may be handled by any trained hospital staff, and there is no need or necessity of a clinical specialist, such as a perfusionist, or cardio technician, to be present for operation of the heart-lung machine. Automated activities, including fastpriming, air bubble detection, air removal system, etc. are necessary for the heart-lung machine to be operated safely without a perfusionist or cardio technician present.

The heart-lung machine is further a mobile, self-contained heart-lung machine and, in some embodiments, comprises a plurality of modules, including for example two or three modules.

Advantageous embodiments of the invention are described in the description, in the drawings and in the dependent claims. Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

FIG. 10b is a schematic cross-sectional view through Line IVa-IVa of FIG. 10a.

FIG. 15 is a support plate of the hose pump.

FIG. 16 is a perspective view of a side of a drive plate of a hose pump.

FIG. 17 is a perspective view of the drive plate of FIG. 16 on that side which is remote from the support plate.

FIG. 18 is a section through the drive plate of FIGS. 16 and 17 along the line VIIVII.

FIG. 19 is an enlarged representation of a coupling device of a hose pump.

DETAILED DESCRIPTION OF THE INVENTION

Figure 1:
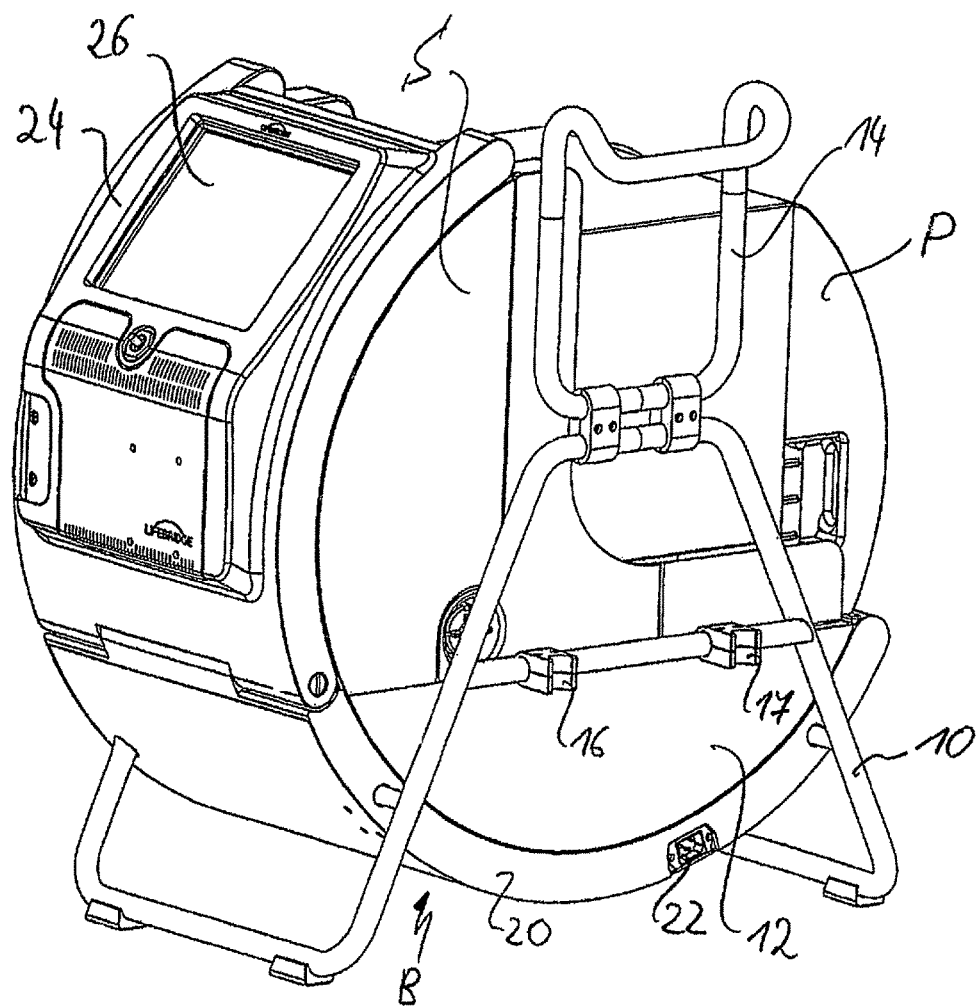
FIG. 1 is a perspective view of a portable heart-lung machine.

In one embodiment, the apparatus and methods involve a heart-lung machine configured for rapid filling and priming by a priming fluid as well as rapid and safe transition to an operational mode. The heart-lung machine comprises a base module and a patient module with pivot means at the base module and/or at the patient module to pivot the patient module relative to the base module about a horizontal axis from a filling position into an operating position.

The patient module can be pivoted in a guided manner relative to the base module by the pivot means, whereby the position and orientation of individual components of the extracorporeal blood circuit is modified so that air bubbles, which cannot escape while the machine is in the filling position, can be removed from the system at or after the transition to the operating position via venting lines. The filling and venting of the patient module can take place in approximately less than 10 minutes, whereas comparable apparatus in accordance with the prior art require approximately 20 minutes for this procedure.

An automated, even quicker priming may be provided by apparatus and methods described in concurrently filed patent applications of the same applicant as the present application having obtained application numbers EP10194069.0, EP10194070.8, and EP10194071.6 (which correspond to U.S. Provisional Application Nos. 61/420,758; 61/420,760 and 61/420,763, filed on even date herewith), which hereby are incorporated herein by reference in their entirety for all purposes. Embodiments of these apparatus and methods when incorporated in the present invention have a number of advantages, including fully automatic priming and air removal, while the below described (90 degree) pivoting process for priming is not necessary.

In one preferred embodiment, there is approximately 90° between the filling position and the operating position, which has the advantage that any air bubbles can reliably escape from the blood-conducting components. A blood reservoir is provided in the patient module and is arranged at an inclination of approximately 45° to the horizontal both in the filling position and in the operating position. This has the consequence that the blood reservoir again has the same orientation relative to the horizontal after a rotation of the patient module by 90° so that the same flow conditions result inside the reservoir before and after the pivoting. A centrifugal pump head having a central inlet and a tangential outlet can be arranged in the patient module such that the inlet is oriented vertically upwardly in the filling position and horizontally in the operating position. In this manner, the pump head can be filled with priming liquid from above without air bubbles remaining in the pump head during this process. It can likewise be advantageous in this process to provide the centrifugal pump head with a tangential outlet, which is arranged at the bottommost position of the centrifugal pump head in the operating position. This ensures that air is not pumped into the patient's circulatory system by the centrifugal pump when the pump is in the operating (operational) position.

The heart-lung machine may comprise, an arterial filter having a venting outlet that can be arranged in the patient module such that the venting outlet is oriented horizontally in the filling position and vertically upwardly in the operating position. Consequently, air inside the arterial filter, which is still present in the filter after the filling with priming liquid, can escape upwardly via the venting outlet after a pivoting into the operating position.

The pivot means provided can be provided in the most varied designs, such as a mount for the patient module pivotally supported at the base module. In this case, the patient module only has to be coupled to the mount in order to permit a guided pivot movement. It is particularly advantageous in this process for the pivot means to include a guide provided at the mount and at the patient module. In this case, the patient module can also be used to ensure the guided pivot movement. It is also possible to connect the patient module to a further module, for example to a control module, and to fasten the unit of the patient module and control module to the mount. In this case, the guide can be provided at the mount and at the control module. It is also possible, for example, to provide a pivot bearing at the base module into which the other module or other modules are inserted.

The patient module is preferably in the operating position after being placed onto the base module since, in this case, a fast removal of the patient module from the base module is ensured without pivoting having to be carried out beforehand. The base module may comprise a device stand, which is provided with a pivotal hook to hang the apparatus on the frame of a patient's bed. The control module and the patient module may also be integrated into a stand alone unit that is operated without the base module. In some embodiments the hook is thus not present, which may provide for an alternative that is advantageous for some transportation situations.

A method for putting the heart-lung machine into operation comprises bringing the patient module into the filling position, in which filling position the blood-conducting components are filled with a priming liquid. The patient module is subsequently pivoted relative to the base module, preferably by about 90°, into the operating position. The pump head provided in the patient module can be driven prior to the pivoting in order to pump the already filled-in priming liquid and thereby to further vent the blood-conducting components.

One embodiment of the heart-lung machine shown in FIGS. 1 to 4, is composed of three modules: a base module B comprising a device stand 10, a control module S and a patient module P comprising extracorporeal blood-conducting components. The patient module P is coupled via latch elements (not shown) to the control unit S to form a unit and this unit, consisting of the control module S and the patient module P is releasably latched to a mount 12 of the base module B.

As FIG. 1 shows, the device stand 10 may be made from tubular material and has a pivotal hooking means 14 at its upper side which is bent to form a hook at its upper side to permit hanging to a frame of a patient's bed. The pivotal hook 14 can be pivoted downwardly by 180° from the position shown in FIG. 1 and can be plugged into two holding clips 16, 17 so that the pivotal hook 14 is not in the way of the mounting of the control module S and of the patient module P.

The device stand 10 is permanently connected to a carrier element 20 of the base module B which has a plug socket 22 for a mains cable. The mount 12 is pivotally supported in the carrier element 20. An operating part 24 is foldably fastened to the left hand side of the carrier element 20 in FIG. 1 and has a touch screen 26 which represents an input and output means for a control device (computer) provided in the base module.

The carrier element 20 and the non-folded operating part 24 form an annular jacket for the unit of mount 12, control module S and patient module P. The operating part 24 must be unfolded open to the left from the position shown in FIG. 1 to mount or remove the unit of control module S and patient module P.

Figure 2:
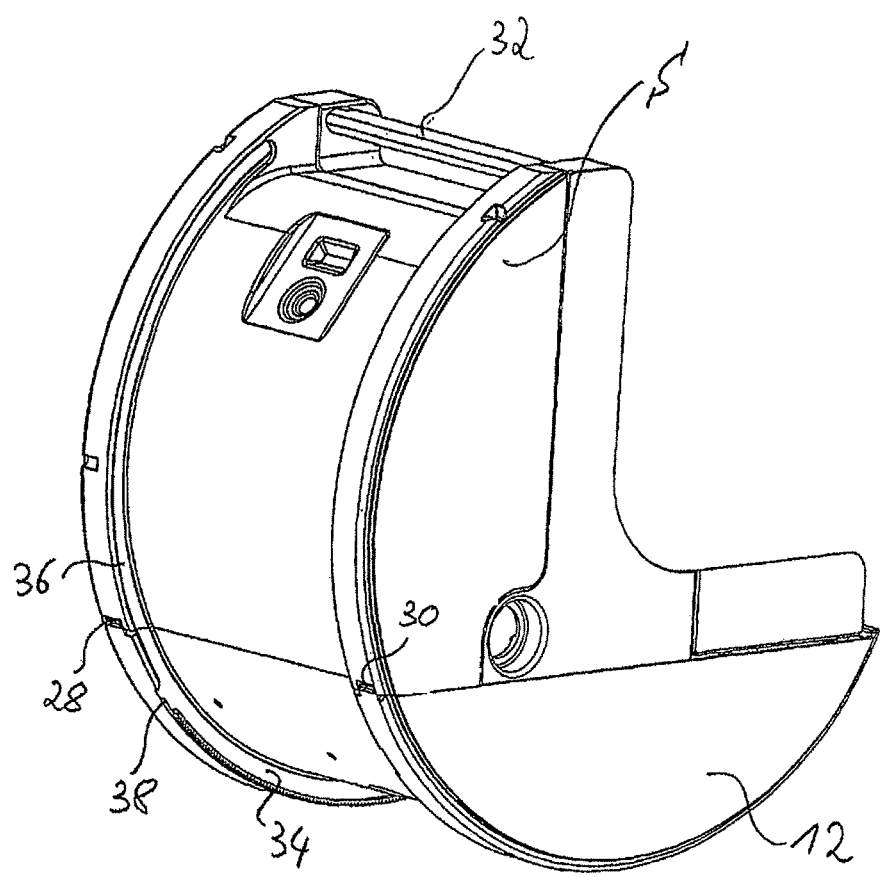
FIG. 2 is a perspective view of the control module of the heart-lung machine of FIG. 1 connected to a mount of the base module.

FIG. 2 shows the mount 12 of the base module B of FIG. 1 to which the control module S is releasably connected by means of latch connections 28, 30. The patient module P is not shown in FIG. 2 for a simplified representation. A unit of control module S and patient module P must always be plugged onto or removed from the mount 12 in operation. The control module S supplements the disk-segment shaped geometry of the mount 12 and a handle 32 is located at the upper side of the control module S with which the unit of control module S and patient module P, on the one hand, but also the whole heart-lung machine, on the other hand, can be handled when the three modules are fastened to one another as shown in FIG. 1.

To pivot the patient module P relative to the base module B about a horizontal axis from a filling/priming position into an operating position, the mount 12 of the base module B is equipped with two guide rails 34 which are parallel, provided at the outer periphery and cooperate with adjoining guide rails 36 of the control module S. The guide rails 34 and 36 form a continuous guide structure with the aid of which the unit of mount 12, control module S and patient module P can be pivoted relative to the base module B. The guide rails 34 of the pivot mount 12 are provided with a cut-out 38 with whose aid the pivot mount 12 can be guided over two rollers (not shown) provided at the carrier element 20 so that the pivot mount 12 can be pivoted on the support element 20 of the base module B. The toothed arrangement recognizable in FIG. 2 serves for the engagement of a damping mechanism ensuring a uniform and damped pivot movement.

To assemble the pivot mount 12 with the support element 20, the pivot mount 12 is first brought into a substantially vertical position and the cut-outs 38 are guided via the rollers (not shown) provided at the carrier element 20, whereupon the pivot mount 12 can subsequently be pivoted into the position shown in FIG. 1. After the folding open of the operating part 24, the previously assembled unit of control module S and patient module P can be latched on the pivot mount 12. To pivot the patient module P from the now present operating position into a filling position, the now formed unit of control module S, patient module P and pivot mount 12 can be pivoted by 90° by pivoting down the handle 32 so that the control module S is in the position in which the pivot mount 12 was previously located. In this filling position, the blood-conducting components of the patient module P are in the position and orientation shown in FIG. 3 with respect to the horizontal.

Figure 3:
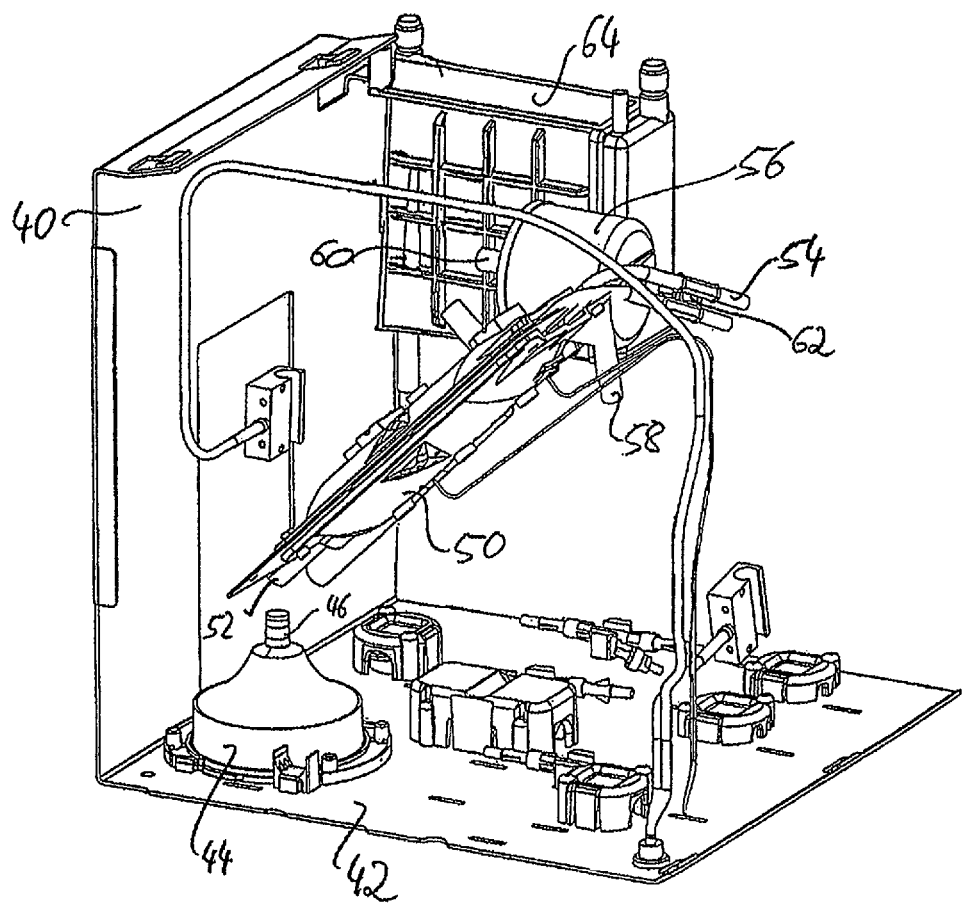
FIG. 3 is a perspective view of some blood-conducting components of the patient module in the filling position.

FIG. 3 shows some blood-conducting components of the patient module, with the patient module P having been rotated about 90° counterclockwise, starting from FIG. 1. The view shown in FIG. 3 corresponds to a view from the other side of the patient module P in comparison with FIG. 1. The wall 40 of the patient module P standing perpendicular in FIG. 3 is thus disposed parallel next to the pivot mount 12, whereas the horizontally oriented wall 42 adjoins the control module S. Furthermore, a plurality of hose connections are now shown in FIG. 3 for a better clear view. Reference numeral 44 designates a centrifugal pump head having a central suction inlet 46 and a radial outlet 48 shown by broken lines in FIG. 4.

An approximately parallelepiped shaped blood reservoir 50 is installed at a position of 45° in the patient module P and its outlet 52 is connected to the inlet 46 of the centrifugal pump head 44 via a hose line (not shown). Venting lines 54 are located at the upper side of the blood reservoir 50. The inlet into the blood reservoir 50 coming from a venous connection is arranged approximately at the centre of the blood reservoir and cannot be seen in FIGS. 3 and 4. It can be recognized in FIGS. 3 and 4 that an arterial filter 56 is provided in the patient module P which has a cylindrical shape, with a tangential inlet 58 and a central axial outlet 60 being provided. A venting connection 62 is provided centrally at the end face of the filter disposed opposite the outlet 60.

Figure 4:
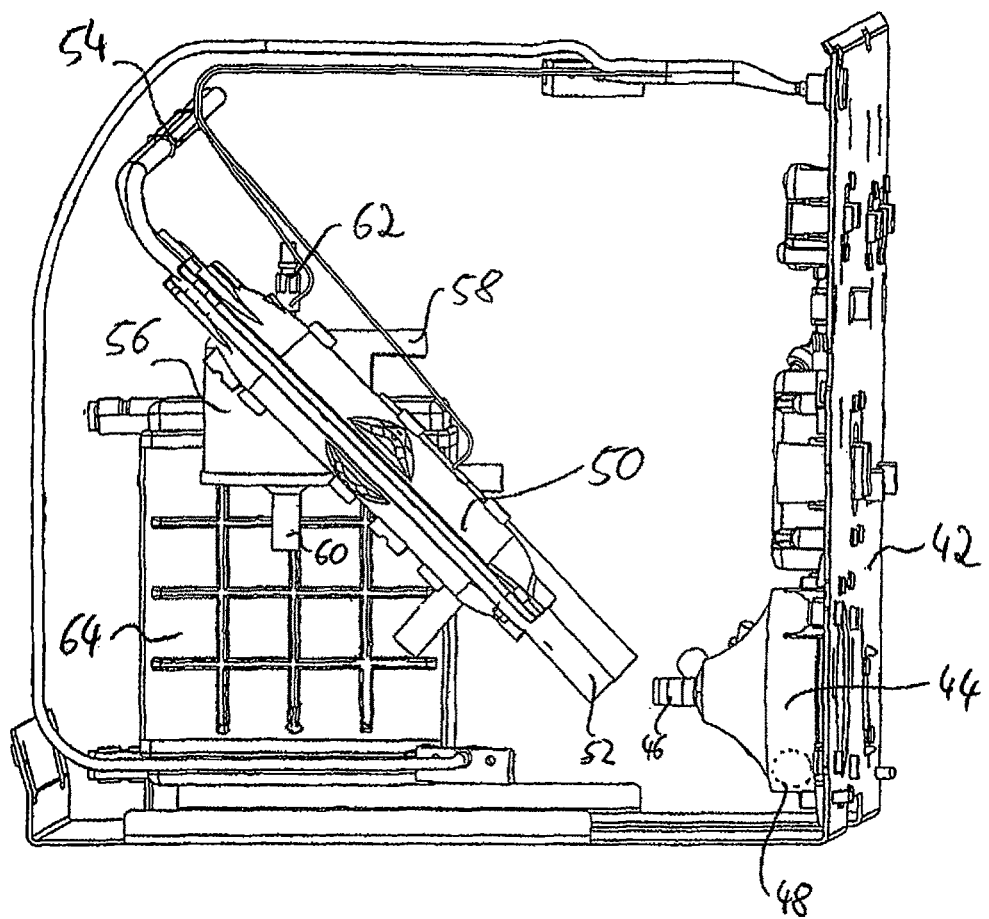
FIG. 4 is the representation of FIG. 3 in the operating position, but viewed from the rear.

Further components shown of the patient module P are an oxygenator 64 and various connection elements which are provided at the wall 42 disposed adjacent to the control module S and which serve for the cooperation with terminals, sensors or plug connections, since all blood-conducting components are provided in the patient module P, whereas control components such as the pump drive, valves and other electrical control elements are arranged in the control module S. FIG. 4 shows the representation of FIG. 3 in the operating position, which corresponds to the representation of FIG. 1 in which the control module S and the wall 42 of the patient module P contacting it are oriented vertically.

As a comparison of FIGS. 3 and 4 shows, there is 90° between the filling position (FIG. 3) and the operating position (FIG. 4), with the blood reservoir 50 provided in the patient module P being arranged in both positions at an inclination of 45° to the horizontal, since it is installed at 45° in the patient module. The centrifugal pump head 44 is arranged such that the central inlet 46 is oriented vertically upward in the filling position (FIG. 3) and horizontally to the side in the operating position (FIG. 4). The outlet 48 (not shown in FIG. 3) of the pump head 44 is arranged at the bottommost position of the centrifugal pump head 44 in the operating position shown in FIG. 4 so that the outlet 48 lies beneath the inlet 46.

The arterial filter 56 is also arranged within the patient module such that the venting outlet 62 is oriented horizontally in the filling position and vertically upwardly in the operating position (FIG. 4). The inlet 58 is oriented vertically downwardly in the filling position and horizontally in the operating position, whereas the outlet 60 is oriented horizontally in the filling position and vertically downwardly in the operating position.

Figure 5:
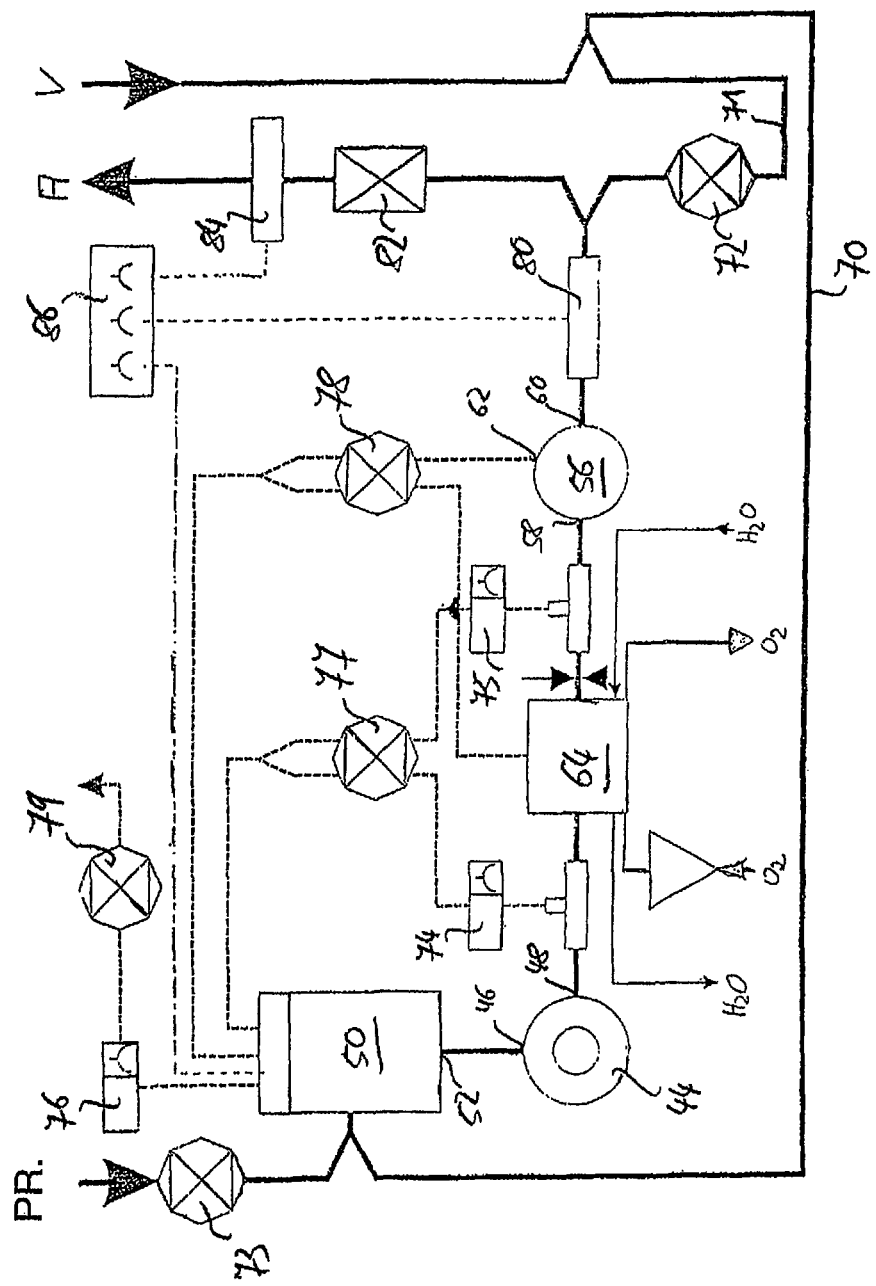
FIG. 5 is a diagram showing the individual components of a heart-lung machine according to the invention.

FIG. 5 shows the different components of the heart-lung machine in accordance with the invention in which the patient blood coming from a venous connection V is guided via a line 70 into the blood reservoir 50 and flows from there via the outlet 52 into the inlet 46 of the centrifugal pump 44. It is pumped from there via the outlet 48 into the oxygenator 64 and flows from there via the arterial filter 56 to the arterial connection A and from there back into the body of the patient. An internal bypass, which can be switched via a valve 72, is designated by reference numeral 71. Reference numeral 73 designates a valve for the inflow line PR with which priming liquid can be guided into the circuit. Reference numerals 74, 75, and 76 each designate pressure sensors. Venting valves are designated by reference numerals 77, 78, and 79, with the valves 77 and 78 switching the vent paths into the upper region of the blood reservoir 50 not filled with blood and the venting valve 79 controlling the venting from the blood reservoir. Reference numeral 80 designates a bubble sensor, which controls an arterial quick action clamp 82 provided in the arterial outlet A if air bubbles are detected. Reference numeral 84 designates a flow sensor and reference numeral 86 an electrical interface. The oxygenator 64 is provided with inflow lines and outflow lines for water and oxygen to effect an enriching of the blood with oxygen and a temperature control of the blood. In some cases the blood temperature may be controlled to maintain normal body temperature, while in other cases, such as slowing the heart rate during CABG, the temperature of the blood may be reduced.

To put the heart-lung machine described above into operation, starting from the representation of FIG. 1, the pivotal hook 14, if present, is first pivoted downwardly by 180° and the operating part 24 is folded to the left. Subsequently, the total unit consisting of the control module S, the patient module P and the pivot mount 12 can be pivoted counterclockwise so that the filling position is reached.

Priming liquid, which first (ct. FIG. 5) fills the blood reservoir and from there the centrifugal pump head 44, is supplied via the connection PR in the filling position. The air located in the hosing is largely removed from the system in this process by the priming liquid arranged above the machine on filling, with air bubbles, however, remaining in the upper region of the arterial filter 56 and in horizontal line portions.

When the blood reservoir 50 is almost filled, the centrifugal pump head 44 is set into rotation comparatively slowly, whereby the priming liquid is pumped through the system and further air residues are removed from the system. After a time period of approximately 20 seconds, further components—such as the oxygenator 64—are also filled with priming liquid so that the pump can be stopped and the unit of the control module S, patient module P and pivot mount 12 can be pivoted back into the operating position.

After these pivoting back by 90°, that air can also escape which had remained in the arterial filter 56 and in horizontal line portions. A complete filling and venting of the patient module can thus be achieved within a time period in the order of magnitude of approximately 6 to 10 minutes.

In one embodiment, the heart-lung machine is a mobile, self-contained heart-lung machine comprising a battery power supply configured to power the heart-lung machine and particularly well suited for use in the field and for emergency use. In another embodiment, the heart-lung machine is a mobile, self-contained heart-lung machine comprising a battery power supply and/or connectors for an external electrical power supply from a transport vehicle with the heart-lung machine configured to operate on battery power and/or the external electrical power supply of the transport vehicle.

In a second embodiment, the apparatus and method of the invention involve a heart-lung machine comprising a blood reservoir, a blood pump, and a bubble detector for the detection of air bubbles between venous and arterial connections to the patient circulatory system. Blood entering at the venous connection is pumped by the blood pump through the blood reservoir and, optionally, through further blood-conducting components via the bubble detector to the arterial connection. An arterial line located downstream of the bubble detector leads to the arterial connection and can be closed by an arterial quick action clamp. If the bubble detector detects an air bubble, the arterial quick action clamp can be closed immediately so that the air bubble cannot enter into the patient's blood circulation from the arterial line. Simultaneously, the blood pump is stopped, a bypass clamp is opened, and the blood pump is re-started so that the blood is guided back into the blood reservoir through a bypass. The blood reservoir is connected to a further pump, which removes air from the top of the blood reservoir where air bubbles collect. As soon as the bubble detector no longer detects any air bubbles, the arterial quick action clamp is opened again and the bypass clamp is closed.

In accordance with an advantageous embodiment of the invention, a blood oxygenator is arranged between the blood pump and the bubble detector. The oxygenator comprises a membrane that is impermeable to air bubbles, which contributes to the elimination of air in the system. An arterial filter configured to collect and hold back microparticles which have entered into the blood as well as gas bubbles can furthermore be provided in front (upstream) of the bubble detector.

It is particularly advantageous for multiple blood-conducting components of the apparatus such as an oxygenator or an arterial filter to be connected to the blood reservoir via a venting line that primarily serves for flushing and venting during a priming process before the apparatus is placed into operation to pump blood. The venting line comprises of clamps that can be used to open and close each venting line during priming. The venting clamps can, however, also be opened briefly during the operation of the apparatus at regular time intervals so that air which has collected in the blood-conducting components is conveyed into the blood reservoir. The air then rises to the surface in the reservoir and can be extracted by a pump provided for this purpose. The venting line is connected to bloodconducting components in each case at the side of the components disposed upwardly during operation so that upwardly rising air bubbles migrate into the venting line. The regular venting of the blood-conducting components prevents the saturation of blood with air and reduces the risk of an air bubble moving up to the bubble detector.

The pump extracting the air from the blood reservoir is preferably a roller pump, which can additionally have a clamping function. Such a pump is described in U.S. patent application Ser. No. 11/366,342 and permits the extraction of air from the blood reservoir with simple means, with it being ensured by the clamping function that no air can flow in the opposite direction, i.e. into the reservoir, even when the pump is switched off.

In accordance with an advantageous embodiment of the invention, the air extracted from the blood reservoir is pumped into an air container arranged downstream of the pump extracting air from the blood reservoir. The total extracorporeal blood circuit thereby remains closed toward the outside. A simple plastic pouch can serve as the air container.

Additional protection from air bubbles in the blood exiting the apparatus can be achieved by configuring the blood reservoir to comprise an inlet region separated from an outlet region by a screen unit which is a membrane permeable for blood, but impermeable for air bubbles.

In accordance with a further advantageous embodiment of the invention, means are provided for the monitoring of the filling level of the blood reservoir. A first sensor is preferably provided which detects whether the filling level reaches a first threshold value. A second sensor detects whether the filling level falls below a second threshold value lying below the first threshold value. The corresponding information can be passed on to an electronic control unit of the apparatus so that the roller pump can be switched on to extract air from the blood reservoir when the filling level falls below the first threshold value. The air which collects in the blood reservoir in bypass operation after detection of an air bubble or on a regular venting of blood-conducting components is thus extracted automatically as soon as a predetermined amount of air is present in the reservoir. As further security, the blood pump can be switched off if the filling level falls below the second threshold value. In this case, an alarm signal is simultaneously output. It is possible for the filling level of the reservoir to fall below the second threshold value, for example, if the venous connection is not properly connected to the patient's blood circulation, but has become loose so that air is pulled into the blood conducting components. In such cases, the described filling level monitoring switches the blood pump off immediately.

In accordance with a further advantageous embodiment of the invention, the bypass clamp is opened at regular time intervals for a short period to flush any pooled blood from the upstream side of the bypass clamp. This prevents coagulation of any pooled blood, which might then enter into the extracorporeal blood circuit after the bypass clamp is opened and, in the worst case, subsequently enter into the patient's blood circulation via the arterial connection.

As a consequence of the described automated safety features present in the heart-lung machine, an intervention by trained medical staff due to an error report is only necessary in an extreme emergency. In the normal case, the apparatus in accordance with the invention can successfully prevent air bubbles from entering into the blood circulation of the patient connected to the apparatus without any human intervention.

A heart-lung machine according to the present invention may be used to provide extracorporeal blood circulation and oxygenation to a patient undergoing conventional or keyhole CABG surgery. A heart-lung machine according to the present invention may also be required in some cases to provide extracorporeal blood circulation and oxygenation during percutaneous angioplasty and/or placement of one or more drug-eluting or nondrug-eluting stents and/or during rotational or laser atherectomy, particularly if complications arise during the procedure such as the heart stopping or complications requiring the sowing or stopping of the heart. In the event of a complication during any of these procedures, the ability to quickly prime the heart-lung machine and bring it into operation is of particular importance. Additionally, no perfusionist is required to prime or operate a heart-lung machine according to the present invention, which expands the conditions and locations under which extracorporeal blood circulation and oxygenation can be safely provided and procedures dependent thereon can be safely performed.

Figure 6:
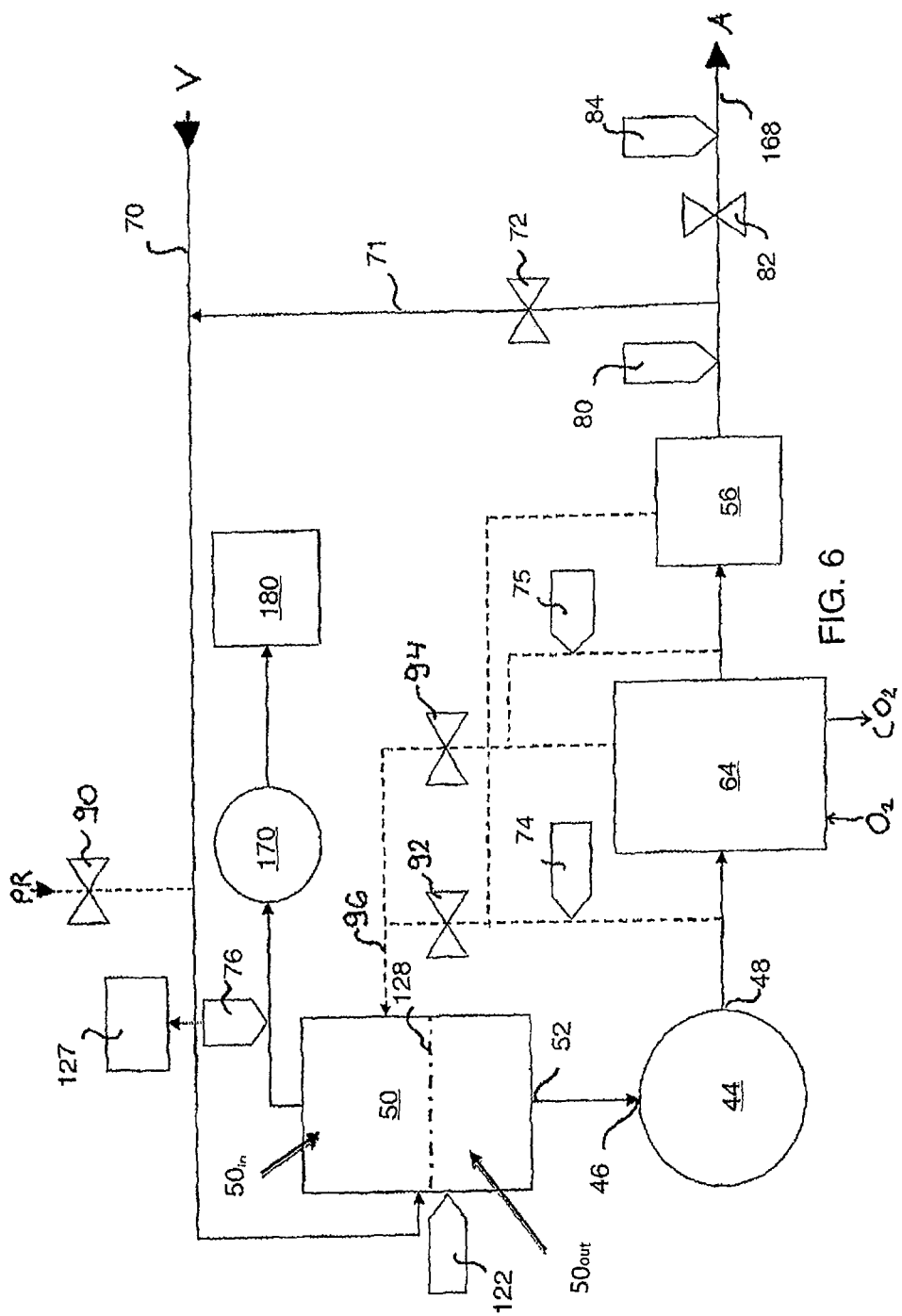
FIG. 6 shows a schematic representation of the individual components of a heartlung machine according to the invention.

FIG. 6 shows a schematic of a heart-lung apparatus according to the invention. Patient blood entering through a venous connection V is guided via a line 70 into a blood reservoir 50 and moves from there through an outlet 52 and into an inlet 46 of a centrifugal pump 44. The inlet 46 is arranged centrally at the pump head of pump 44 and blood is pumped through a tangential outlet 48 arranged at the bottom most point of the pump head of the centrifugal pump 44 and into an oxygenator 64 to which an oxygen supply line is connected. Blood enriched with oxygen is subsequently filtered in an arterial filter 56 and finally flows, in the normal case, through an arterial line 168 and via an arterial connection A back into the patient.

The blood reservoir 50 is split into an inlet region 50 in and a separate outlet region 500 out by a membrane 128 that is permeable for blood, but prevents air bubbles entering into the outlet region from the inlet region.

A bubble detector 80 is arranged between the arterial filter 56 and the arterial connection A. As long as it does not detect any air bubbles, an arterial clamp 82 in the arterial line 168 remains open, while a bypass clamp 72 remains closed. Blood flow can be continuously monitored by flow sensor 84, which measures blood flow in the arterial line 168.

If an air bubble is detected in the bubble detector 80, the arterial clamp 82 is closed immediately. The reaction path between the bubble detector 80 and the arterial clamp is configured to be long enough that a detected air bubble cannot reach the clamp before the clamp is closed. The clamp 82 is preferably a fast-closing clamp, which closes in less than 300 ms, as described in co-assigned U.S. patent application Ser. No. 11/366,914. Clamp 82 is also called quick action clamp herein. The sufficiently long reaction path and the speed with which the clamp closes advantageously prevents any air bubble detected by the bubble detector 80 from reaching the arterial connection A. Simultaneously, the blood pump 44 is stopped, the bypass valve or clamp 72 is opened, and the blood pump 44 is restarted, so that the blood, together with the detected air bubble, flows via a bypass 71 back into line 70 and into the blood reservoir 50.

In the blood reservoir 50, air bubbles rise upwardly so that blood is located at the bottom in the reservoir 50 out, and air collects at the top 50 in. Means 122 for the monitoring of the filling level of the blood reservoir are electronically coupled, for example via an electronic control unit, to a hose roller pump 170 configured for the extraction of air from the reservoir. The hose roller pump 170 may be, for example, a hose pump as disclosed in U.S. application Ser. No. 11/366, 342. As soon as the monitoring means 122 of the filling level of the blood reservoir 50 reports that the filling level has fallen below a first threshold value, the hose roller pump 170 is switched on to remove air from the top of the reservoir 50 in and pump the air into a waste container 180. The hose roller pump 170 has a clamping function so that it acts as a clamp if it is not actively pumping to prevent a backflow of air into the blood reservoir 50. If the filling level of the blood reservoir falls further, despite the removal of air by the hose roller pump 170, below a second threshold value, the centrifugal pump 44 is switched off and an alarm, for example an audible and/or visible signal is output.

The oxygenator 64 and the arterial filter 56 are each connected to the upper region of the blood reservoir 50in by a venting line 96 provided with venting valves 92, 94. The venting line first serves for the flushing and venting of the heart-lung machine during a priming procedure before it is put into operation. In this procedure, a priming liquid is filled in via a priming connection PR and priming circuit (dashed line passing through valve 90) and the extracorporeal blood circuit is vented. The venting clamps 92 and 94 are normally closed during the operation of the heart-lung machine but are, however, opened briefly at regular time intervals, for example every 10 to 15 minutes, so that accumulated air in the oxygenator or the arterial filter is guided into the reservoir 50 for removal from the system.

Pressure sensors 74, 75 monitor the pressure before (upstream of) and after (downstream of) the oxygenator. The measured values of the pressure sensors are forwarded to a pressure monitoring unit 127 via a connection (not shown for reasons of clarity). An abnormal increase in the pressure drop at the oxygenator 64 can be an indicator of clogging by coagulated blood, and a need for action may be indicated, for example, by triggering an audible and/or a visual signal. Additionally, the extraction pressure at which blood is extracted from the patient into the line 70 is monitored using pressure sensor 76, which measures the pressure in the line connecting the blood reservoir 50 and the hose roller pump 170. The measured result is likewise passed on to the pressure monitoring unit 127.

To avoid coagulation of standing or pooled blood in the bypass 71 in FIG. 6 beneath the bypass clamp 72 while the arterial clamp 82 is open and the bypass clamp 72 is closed, the bypass clamp 72 may be opened at regular time intervals for a short time to periodically flush the bypass 71.

Arterial quick action clamp 82 shown in FIG. 6 is preferably a fast closing clamp as shown in FIGS. 7-11. The sectional view of FIG. 7 corresponds to the cross-section indicated by A in FIG. 9. The hose 201 contacts a wall 203, which is formed for example by the rear wall of a housing part receiving the hose. A clamp jaw 205 is configured to be brought into a clamping position in the arrow direction by the fast closing clamp, pinching the hose 201 closed.

A holding apparatus 207 comprises an inner hollow space in which the clamp jaw 205 is guided. In the embodiment shown, the clamp jaw 205 is an internal piston and the holding apparatus 207 is an external piston, with the internal piston 205 being displaceably received in the external piston 207 and the external piston 207 being displaceably received in a housing 209. A spring 217 is supported against a seat 216 inside the external piston 207 and a seat 218 is supported at the external periphery of the internal piston 205, said spring being under compressive tension in the open position of the internal piston shown in FIG. 7.

The spindle 219 of a spindle drive comprises an external thread 221 in the region in which it engages into the external piston 207, which has a corresponding mating thread at the internal periphery where the spindle 219 passes through it. The spindle 219 is rotatably held in the housing 209 in a bearing 223. The spindle is connected to a toothed wheel 225 via the grub screw 227. The toothed wheel 225 meshes with a toothed wheel 229 which, in turn, meshes with a toothed wheel 231 that is connected via a grub screw 233 to the axis of an electric motor 235 which is fixedly installed in a holding plate 237.

The toothed wheel 229 is rotatably supported in the holding plate 237. The housing 209 is permanently connected to the holding plate 237. A hollow space 215 is located in the external piston 207 and balls 213 can partly enter into it, which project radially out of the internal piston 205 in the latched state.

Figure 7:
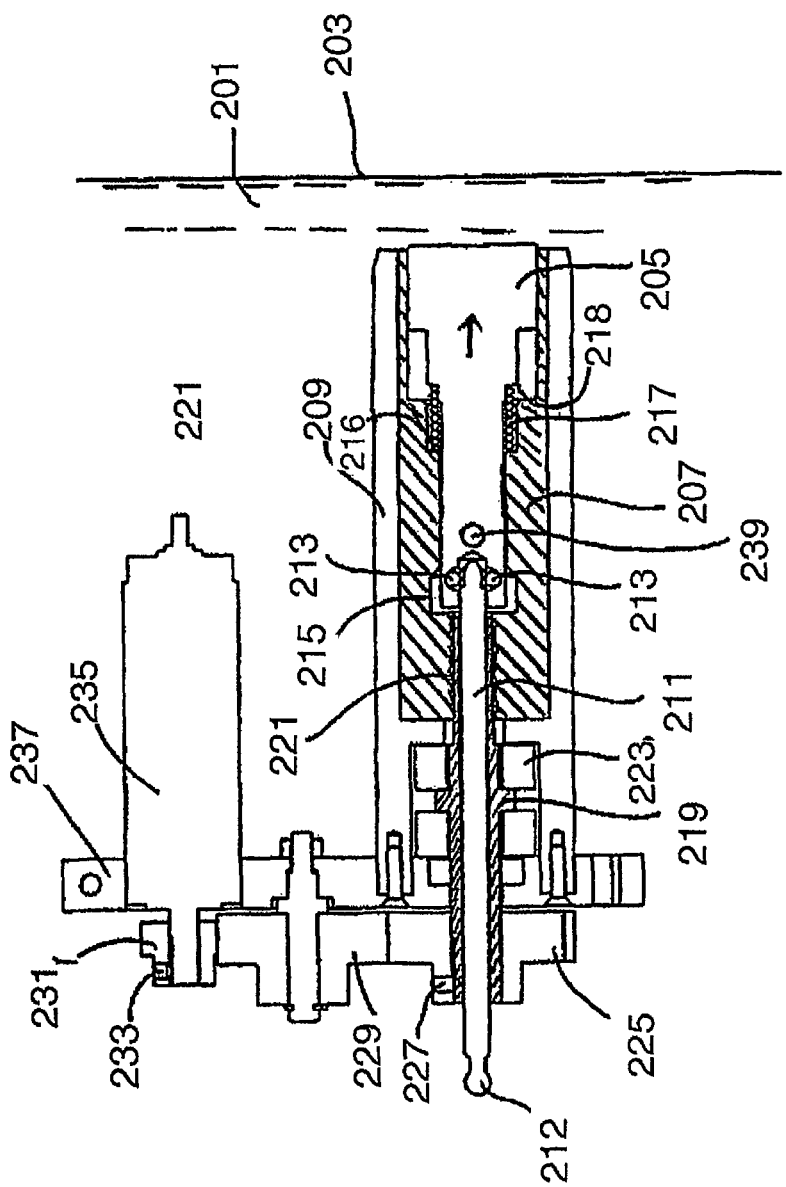
FIG. 7 is a lateral section through a fast closing (quick action) clamp.
Figure 8:
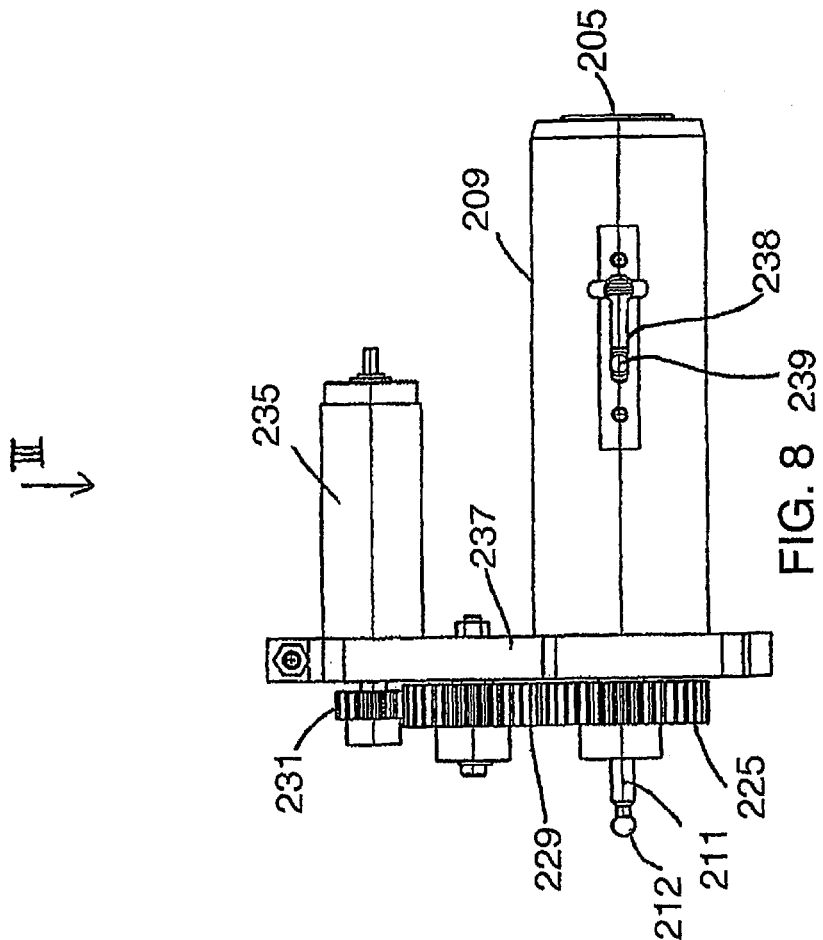
FIG. 8 is a lateral plan view of a fast closing clamp.
Figure 9:
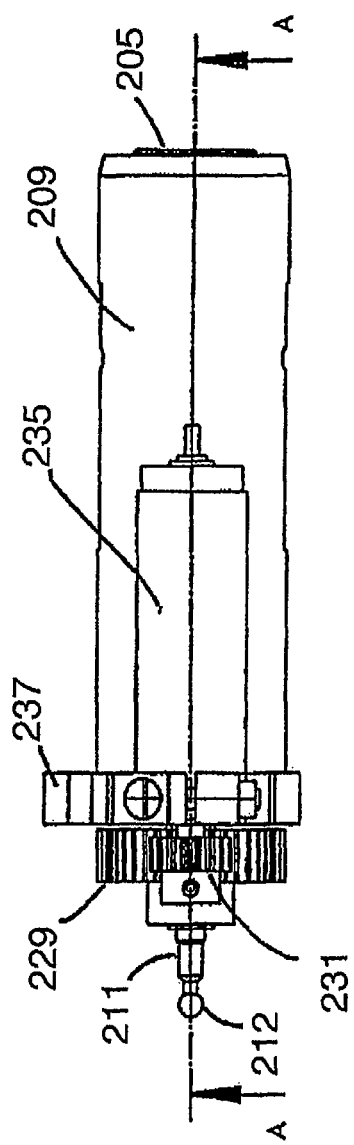
FIG. 9 is a plan view in the direction III indicated in FIG. 8.

FIG. 8 shows the fast closing clamp of FIG. 7 in a lateral plan view. The direction of view visible in the plan view of FIG. 9 is indicated by III in FIG. 9. The internal piston 205 comprises a radially outwardly extending abutment bar 239, which is guided in an elongate hole 238 of the housing 209 (FIG. 8).

Figure 10A:
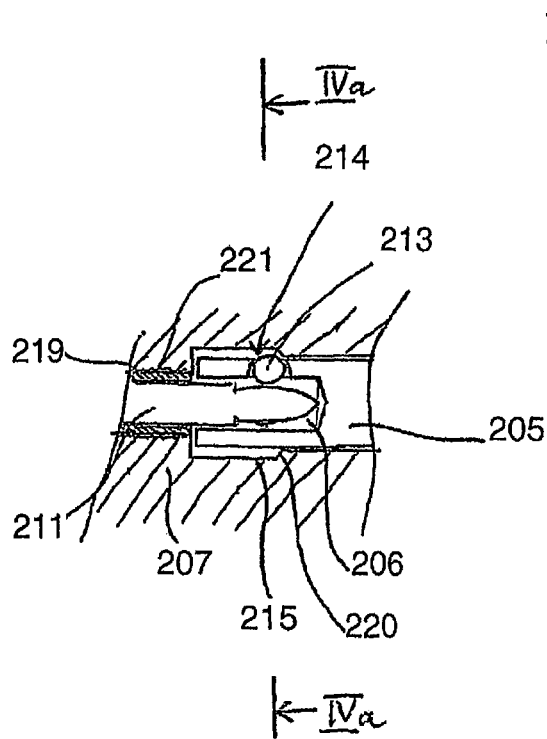
FIG. 10a is a detail of the sectional view of FIG. 7.

FIG. 10*a* shows a detail of FIG. 7 in the region of the latch device between the external piston 207 and the internal piston 205. The latched state is also shown in FIG. 10*a*. The tip of the blocking bar 211 lies in the axial cut-out 206 of the rear part of the internal piston 205. In this process, the tip presses balls 213 outwardly through radial openings 214 in the internal piston 205, which partly enclose the balls 213. The tip of the blocking bar 211 is made in ball shape and tapered toward the front so that it can easily be pushed between the balls 213. In the embodiment shown, three of the radial openings 214 are provided with corresponding balls 213 at an angle of 120° to one another. The two other openings are therefore not visible in the sectional representation of FIG. 10*a*.

The balls 213 engage into a cut-out 215 in the external piston 207. In the state shown, the internal piston 205 cannot move out of the external piston 207 to the right since the balls 213 are fixed in the cut-out 215 of the external piston 207. If the blocking bar 211 is pulled out of the axial cut-out 206 of the internal piston 205 to the left, the balls can move into the axial cut-out 206 and the internal piston 205 can be moved out of the external piston 207 to the right by the force of the spring 217. The inward movement of the balls 213 is in particular facilitated by the chamfering 220 of the cut-out 215. The right hand end of the spindle 219 can be recognized in FIG. 10*a* with the thread 221, which meshes in an internal thread of the external piston 207.

Figure 10B:
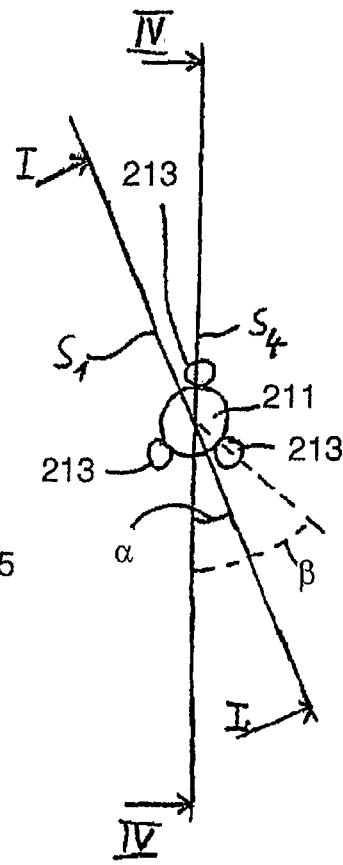

Whereas FIG. 10*a* shows a section through the fast closing clamp in which a ball 213 is sectioned precisely at the center. FIG. 7 shows a section in which no ball 213 is precisely cut. In this respect, the sectional planes of FIG. 7 and of FIG. 10a are tilted with respect to one another by 30° around an axis which is, for example, defined by the blocking bar 211. This relationship is illustrated in FIG. 10b, which shows a cross-sectional view through Line IVa-Iva as labeled on FIG. 10a. A view in an axial direction of the tip of the blocking bar 211 and of the balls 213 is shown in a schematic representation in FIG. 10b. 51 shows the sectional plane of FIG. 7, while 54 shows the sectional plane of FIG. 10a. The direction of view of the sectional plane, which is the subject matter of FIG. 7, is designated by the arrows I in FIG. 10b. The direction of view of the sectional plane, which is the subject matter of FIG. 10a, is designated by the arrows IV in FIG. 10b. The angle J3 indicated amounts to 60 degrees, whereas the tilt angle of the sectional plane amounts to 30 degrees.

Figure 11:
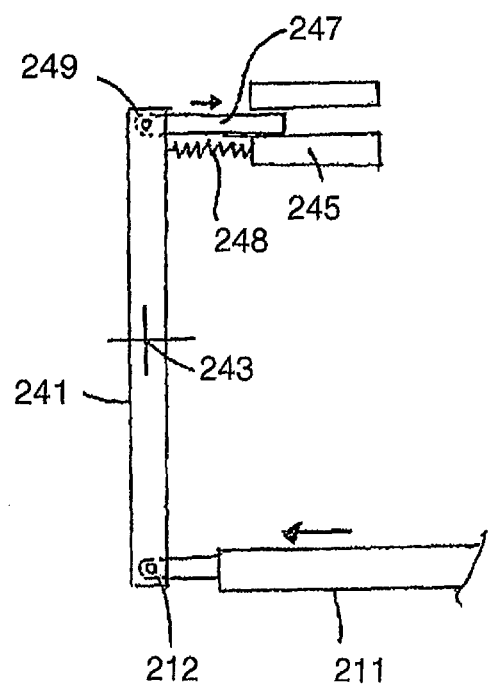
FIG. 11 is a schematic of a fast closing clamp not shown in FIGS. 7-9.

FIG. 11 shows a part of the quick action, fast closing clamp not shown in FIGS. 7-10a, which is a mechanism that moves the blocking bar 211 in the axial direction. The blocking bar 211 is connected via a hinge point 212 to a rocker 241, which is rotatably supported at the point 243. This rocker is connected via a hinge point 249 to a metallic actuation bar 247, which projects into an electromagnet 245. In this arrangement, the bar 247 moves to the right on a flow of current through the electromagnet 245. The rocker rotates around the center of rotation 243 and moves the blocking bar 211 to the left in the representation of FIG. 11. A compression spring 248 biases the rocker 241, the actuation bar 247, and the blocking bar 211 in the direction of their positions of rest when the electromagnet 245 again has no current. The force of the electromagnet 245 acts against the spring force of this spring 248.

When a bubble is detected in the hose 201, a signal is transmitted to put the electromagnet 245 under current for approximately 50 ms so that the actuation bar 247 moves into the electromagnet. The rocker 241 rotates around the center of rotation 243 and pulls the blocking bar 211 to the left. The blocking rod 211 thereby moves out of the axial hollow space 206 (FIG. 10a) of the internal piston 205. The internal piston 205 is urged in the direction of the arrow (FIG. 7) by the spring force of the spring 217. Since the blocking bar 211 no longer blocks the axial hollow space, the balls 213—facilitated by the chamfer 220—escape back into this hollow space 206 and the latch connection between the internal piston 205 and the external piston 207 is cancelled. The spring force of the spring 217 drives the internal piston 205 against the hose 201 and pinches it off against the rear wall 203 of the passage conducting the hose. It is, for example, sufficient to operate the electromagnet only for approximately 50 milliseconds to trigger this action. The hose is pinched off after only around 100 milliseconds. The abutment bar 239 guided in the longitudinal hole 238 in the housing 209 prevents the internal piston 205 from being able to completely exit the housing 209 on an unintentional triggering.

To move the internal piston back into its open position, the electric motor 235 is switched on. The spindle 219 is driven via the toothed wheels 231, 229, and 225. The external piston 207 moves axially to the right out of the housing 209 by the spindle rotation. The internal piston 205 is in the meantime still supported against the hose 201 or the rear wall 203 of the passage. As soon as the external piston 207 and the internal piston 205 are again completely pushed onto one another, the radial openings 214 in the internal piston 205 are again in the region of the cut-out 215 inside the external piston 207. The tip of the blocking bar 211 can again push between the balls 213 which are in turn moved radially outwardly through the openings 214 in the internal piston 205. The blocking bar 211 is pushed into the axial cut-out 206 of the internal piston 205 by the action of the spring 248 which acts on the rocker 241 for this purpose. The balls 213 again engage into the cut-out 215 in the external piston 207 as is shown in FIG. 10a and latch the external piston 207 and the internal piston 205.

If the electric motor 235 is operated in the reverse direction, the spindle 219 pulls the external piston 207 to the left in the representation of the Figures. The internal piston 205 is also moved back due to the latching of the internal piston 205 in the external piston 207 and the fast closing clamp again moves to its open position. The spring 217 again starts to tense while the external piston 207 is again pushed over the internal piston 205 and stores energy for a new triggering process. It is possible in this way to trigger a further pinching process as required on the returning of the internal piston 205 together with the external piston if e.g. a bubble is again detected in the extracorporeal circuit during the return of the internal piston 205.

Figure 12:
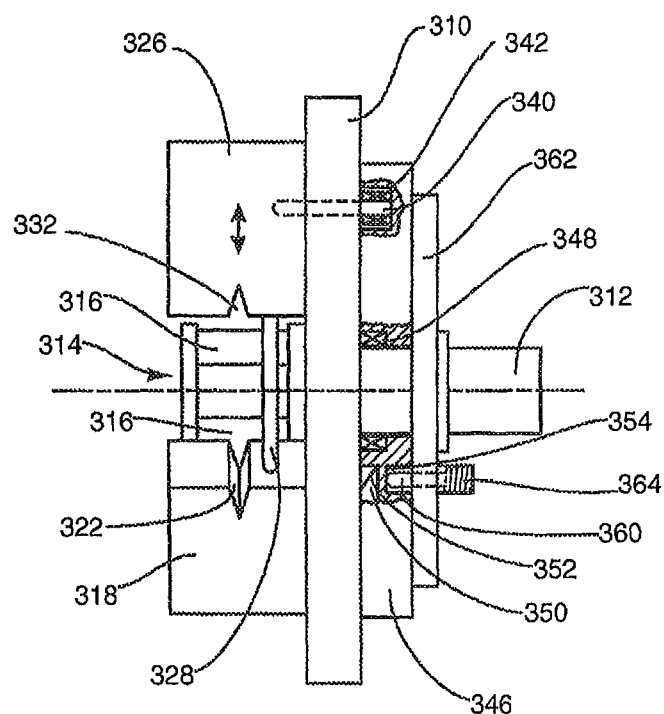
FIG. 12 is a side view of a peristaltic hose pump.

The hose roller pump 170 in FIG. 6 is preferably a peristaltic hose pump as shown in FIGS. 12-19. The pump, as shown in FIG. 12, comprises a support plate 310, which can be installed in a fixed position, and a bore through which a drive shaft 312 is rotatably inserted. The right end of the drive shaft 312 in FIG. 12 can be driven by a drive (not shown), for example by an electric motor, whereby a rotor 314 attached to the left end of the drive shaft 312 in FIG. 12 likewise rotates. The rotor 314 has a plurality of rollers 316 which are distributed over its periphery and which serve in a known manner to press fluid (e.g. air or blood) through a flexible hose (not shown).

Figure 13:
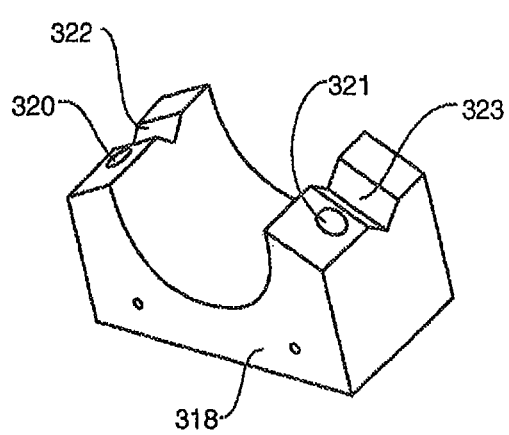
FIG. 13 is a mating piece of a hose pump.

A mating piece 318, shown in a perspective view in FIG. 13, is screwed beneath the rotor 314 to the left side of the support plate 310 in FIG. 12 and has two vertical blind bores 320 and 321, on the one hand, and two V-shaped grooves 322 and 323, on the other hand, which extend at an angle to the horizontal and extend inside one and the same vertical plane. The mating piece 318 furthermore has an approximately semi-circular opening in which the rotor can rotate freely.

FIG. 12 shows that a support element 326 above the rotor 314, which is movable in the direction of the double arrow by a predetermined distance in the direction toward the rotor 314 or by a predetermined distance away from the rotor 314. FIG. 12 shows the pump with the support element completely moved away from the rotor 314 by the predetermined distance.

Figure 14:
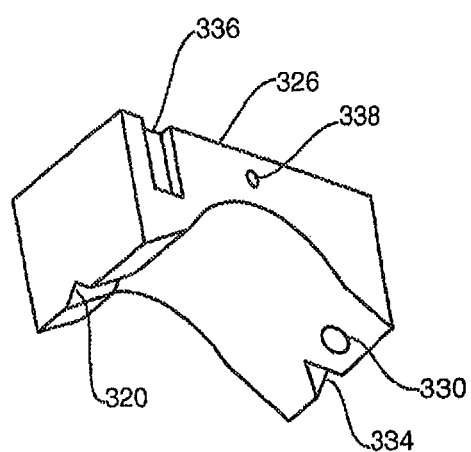
FIG. 14 is a support element of a hose pump.

Two guide pins 328 (only one is shown in FIG. 12), which are inserted into the blind bores 320 and 321 of the mating piece, guide the support element 326. As FIG. 14 shows, the support element 326 likewise has two blind bores 330 (only one is shown in FIG. 14) so that the support element 326 is guided by the guide pins 328. FIG. 14 shows that the support element 326 also has two V-shaped grooves 332 and 334 which, together with the grooves 322 and 323 of the mating piece 318, form a clamping device in which the hose can be clamped by a movement of the support element in the direction toward the rotor. A groove 336 provided at the rear side of the support element 326 serves for the insertion of a metal piece to permit a contact free position detection with the help of a sensor (not shown). A blind bore 338 is provided centrally at the rear side of the support element 326. A pin 340 is inserted into this blind bore, as shown in FIG. 12, extending through an elongate hole 341 in the support plate 310 and simultaneously serving as an end abutment for the movement of the support element 326. The pin 340 projects somewhat from the support plate 310 on the side thereof opposite to the support element 326 and the projecting end of the pin 340 is inserted into a plain bearing 342 which is movable in a spiral groove 344 (FIG. 17) of a drive plate 346.

The drive plate 346 is shown in more detail in FIGS. 16-18 and is placed freely rotatable onto the drive shaft 312 via a plain bearing 348. FIG. 17 shows a view of that side of the drive plate 346 which faces the support plate 310. The spiral groove 344 extends from the outer rim of the drive plate 346 in the direction of the center, with the spiral groove extending over an angle of somewhat more than 180°. A ring groove 350 is provided at the interior of the spiral groove 344 and receives a fixed position cam guide 352, which is made integrally with the support plate 310 (FIG. 15). FIGS. 15 and 19 show that the fixed position guide cam 352 has a rising and a falling flank of the same gradient. In this process, the guide cam 352 is curved in the peripheral direction such that it fits into the ring groove 350 of the drive plate 346.

FIG. 16 shows the side of the drive plate 346 disposed at the bottom in FIG. 17. A curved recess is provided at this side of the drive plate 346, which has two guide chamfers 354 and 356 whose lowest point forms an opening 358 through which a passage into the ring groove 350 is created. This passage serves for the passing through of a drive pin 360, which serves as a coupling member between the drive shaft 312 and the drive plate 346.

FIG. 12 shows that a drive plate 362 is rotationally fixedly connected to the drive shaft 312, with the drive pin 360 being resiliently supported in a sleeve 364 provided at the drive plate 362 such that it is displaceably supported against the force of the spring in the axial direction of the drive shaft 312. When the drive shaft 312 thus rotates, the drive plate 362 and also the drive pin 360 rotate together with it. In this process, the drive pin 360 presses against the drive plate 346 due to the spring and the front end of the drive pin 360 runs on the drive plate on an orbit which is indicated by a broken line in FIG. 16. If, in this process, the drive pin 360 moves into the region of the guide chamfers 354 and 356, the front end of the drive pin 360 moves on these guide chamfers until it moves through the opening 358 in the drive plate.

The starting position is the situation shown in FIG. 12 in which the support element 326 has been moved away from the rotor 314 by the predetermined distance. In this position, the drive pin 360 is located in the situation shown in FIG. 19 in which it projects through the opening 358 in the drive plate 346 and its front end lies on the fixed position cam guide 352. If, in this process, the drive shaft 312 and thus the drive wheel 362 are moved against the arrow direction S, the drive pin 360 is moved to the right in FIG. 19 and first runs on the fixed position cam guide 352 and subsequently on the guide chamfer 356 of the drive plate 346 which merges constantly into the left hand flank of the fixed position cam guide 352. Subsequently, the drive pin 360 runs on the orbit shown by a broken line in FIG. 16 until it again moves toward the guide chamber 354 and slides along on this until the situation of FIG. 19 being the result. This means that the drive shaft can be rotated as desired against the arrow direction shown in FIG. 19, without the drive plate 346 moving.

After a flexible hose has been inserted into the intermediate space between the support element 326 and the rotor 314, the direction of rotation of the drive shaft 312 is reversed and now runs in the direction of the arrow S shown in FIG. 19. However, this means that the drive pin 360 abuts the lower end of the guide chamfer 354, so that, on a further rotational movement, the drive plate 346 is taken along by the drive pin 360 and likewise rotates in the direction of the arrow S. In this process, the front end of the follow pin runs along the falling flank of the cam guide 352 until it revolves on the orbit shown by a broken line in FIG. 15.

On this rotation of the drive plate 346, the plain bearing 342 simultaneously runs in the spiral orbit 344 and thereby moves in the direction of the axis of rotation, whereby the pin 340 in the elongate bore 341 is likewise moved in the direction of the axis of rotation. Consequently, the support element 326 is moved by the predetermined distance in the direction toward the rotor 314 such that the flexible hose (not shown) is respectively clamped between the V grooves 322 and 332, and 323 and 334. At the same time, the hose is clamped between the support element 326 and the rotating rollers 316 of the rotor 314 so that a pump effect is achieved.

After a complete revolution of the drive pin 360 on the orbit shown in a broken line in FIG. 15, said drive pin moves from the right side in FIG. 19 back up to the cam guide 352 and subsequently slides upwardly on this until the front end moves onto the guide chamfer 354 of the drive plate 346 constantly adjoining the cam guide 352 at this point in time. The drive pin 360 then slides further upwardly on this guide chamfer 354 until the front end of the drive pin 360 revolves on the orbit shown in a broken line in FIG. 16. When the drive shaft is rotated further in the direction of the arrow S, the drive pin 360 can revolve for any desired length of time without effecting a movement of the drive plate 346. Only when the direction of rotation is reversed again does the drive pin 360 again couple with the drive plate 346 in that it moves through the opening 358 and slides downwardly on the fixed position cam guide 352. The front end of the drive pin 360 subsequently again revolves once on the orbit shown by a broken line in FIG. 15 until the situation shown in FIG. 19 is the result.

One important advantage of the present apparatus and methods over existing apparatus and methods is the ability to quickly provide extracorporeal blood circulation and oxygenation without the need for a specially trained operator. Quickly and automatically priming the apparatus and then placing the apparatus into an automated operational mode required is enabled by the safety features described herein. Various combinations and configurations of Quick-action (fast closing) clamps, vent lines, filters, air removal pumps, and other components achieve a level of safety that permits the automation of the heartlung machine and methods involving an automated heart-lung machine.

Figure 20:
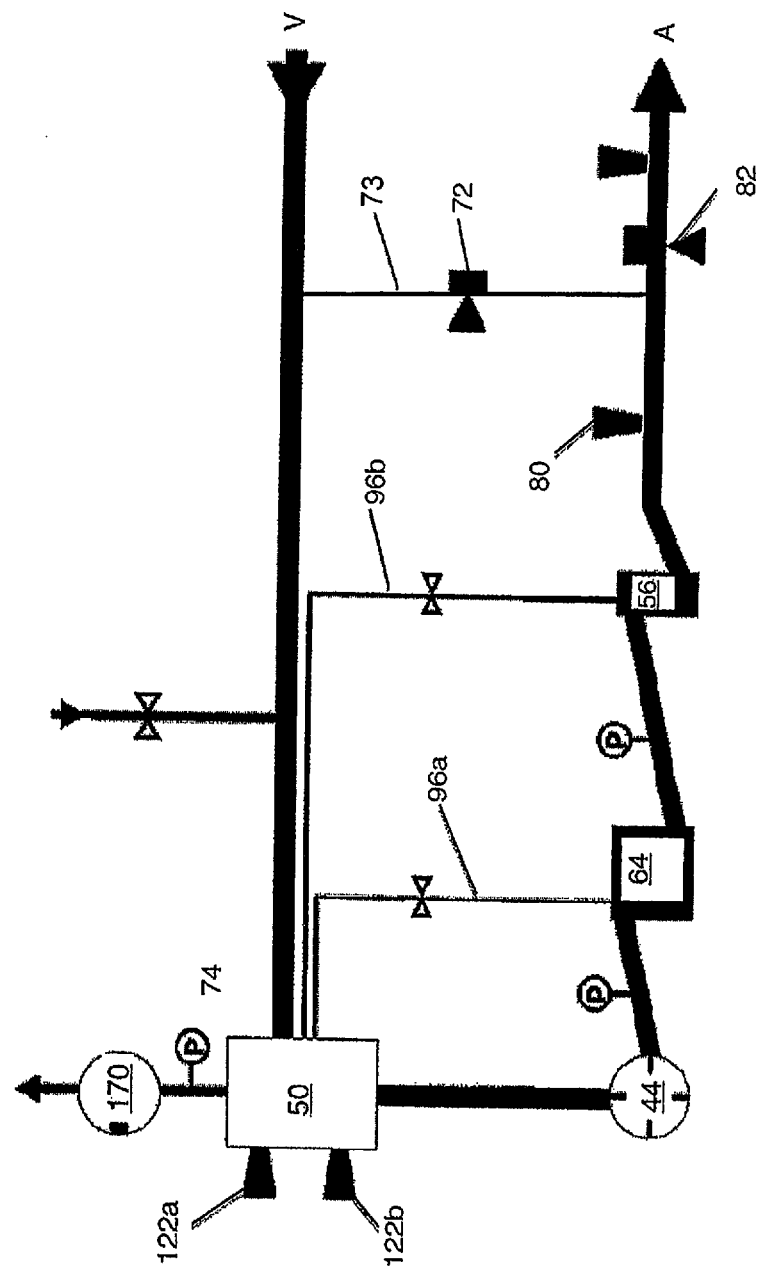
FIG. 20 is a diagram of an exemplary multi-stage air removal system.

FIG. 20 shows a preferred embodiment of a multi-stage air removal system providing a level of safety that permits automated extracorporeal blood circulation and oxygenation. A screen filter with a suitable pore size, such as 120 IJm, separates the blood reservoir 50 into two sections (FIG. 5). Air bubbles having a diameter of greater than 120 IJm cannot pass through the screen from the venous blood input section of the reservoir to the output section of the reservoir.

An upper level fill sensor 122a capable of distinguishing between gas (air) and liquid (blood) is connected to a roller pump 170 configured to remove air from the inlet portion of the blood reservoir. When the upper level sensor 122a detects a liquid, the roller pump 170 is inactive. When the level of blood falls below the level of the upper fill sensor 122a, the sensor detects air and sends a signal to the roller pump 170, causing the pump to remove air from the top of the reservoir. Removing air from the reservoir results in a relative negative pressure within the reservoir that increases the rate at which blood is drawn into the inlet of the reservoir from the venous blood source.

A lower level fill sensor 122b capable of distinguishing air from blood is connected to a centrifugal pump 44 configured to pump blood from the reservoir 50 to an oxygenator 64. As long as the lower level fill sensor 122b detects blood, blood is pumped from the reservoir 50 to the oxygenator 64. When the lower level fill sensor 122b detects air, it sends a signal to the centrifugal pump 44, causing the pump to immediately stop pumping blood from the reservoir. This prevents the centrifugal pump from emptying the reservoir and pumping air into the downstream blood conducting components of the heartlung machine.

The centrifugal pump 44 has a central inlet and a tangential outlet at the lowest point of the pump head with respect to gravity. Should air enter the inlet of the pump, the rotation of the pump causes liquid in the pump to move toward the outer wall of the pump head leading to the outlet while any air is moved toward the center of the pump head and prevented from reaching the outlet. Any air in the pump remains in the top center portion of the pump head, which successfully prevents even a small volume of air from reaching the downstream blood conducting components of the heart-lung machine.

The oxygenator 64 has a separate ventilation system where air rises to and is removed from the highest point of the oxygenator 64. A vent line (purgeline) 96a is connected to the top of the oxygenator and configured to carry the air away from the oxygenator. In a preferred embodiment, the oxygenator vent line 96a carries air from the oxygenator 64 to the blood reservoir 50 as shown in FIG. 20.

Oxygenated blood moves from the oxygenator 64 to a vented arterial filter 56. A vent line 96b (purge line) is connected to the highest point in the arterial filter 56 and removes air that is trapped by the filter. In a preferred embodiment, the arterial filter vent line 96b carries air from the filter 56 to the blood reservoir 50.

The air bubble sensor 80 (detector) is positioned downstream of the arterial filter 56 and communicates with a quick-action clamp 82 positioned on the arterial line leading to the arterial connection A and to a bypass clamp 72 located on a bypass line (not shown). In normal operation without air bubbles, the quick-action clamp 82 is open and the bypass clamp 72 is closed. In response to the detection of an air bubble by the bubble sensor 80, the quick-action clamp 82 on the arterial line closes immediately. Then the bypass clamp 72 on the bypass line opens to divert blood flow away from the arterial connection A and back to the blood reservoir 50 through the bypass line. As the bypass clamp is not a quick action clamp, but an ordinary hose clamp, it opens much slower than the quick action clamp 82 closes. Therefore, when the quick-action clamp 82 is activated, the blood pump is simultaneously stopped, and the bypass clamp is "slowly" opened. After a short delay period, when the bypass clamp is open, the blood pump is re-started. This is made to ensure that the running blood pump does not generate undesired high pressures in the blood conveying system against the closed quick action clamp 82 and the closed bypass clamp 72. Thus leakage caused by overpressure in the system is effectively avoided. Once no air bubbles are detected in the bypass flow by the air bubble sensor and a predetermined time interval has elapsed, the first and second quick-action clamps revert to their normal operating positions.

A method according to the present invention comprises priming, or filling, the heart-lung machine with a priming fluid such as sterile saline. Once initiated, the priming can take place in an automated manner without human intervention. When primed and operational, the machine is fluidly coupled to the circulatory system of the patient through a vein to the venous coupling of the machine and through an artery to the arterial coupling of the machine.

The heart of the patient may optionally be slowed or stopped, if necessary. The blood returned to the patient is enriched with oxygen. In some cases the blood temperature may be controlled to a body temperature below normal body temperature and above a temperature where organs may be damaged. Such a temperature range may currently be achieved by placing the patient, or only the heart, in an ice bath during surgery. Controlling the blood temperature, and perhaps cooling the blood before re-entering it into the patient via the venous vessel connection, is an elegant solution whereby the body temperature and/or the heart temperature is much better controlled.

Figure 21:
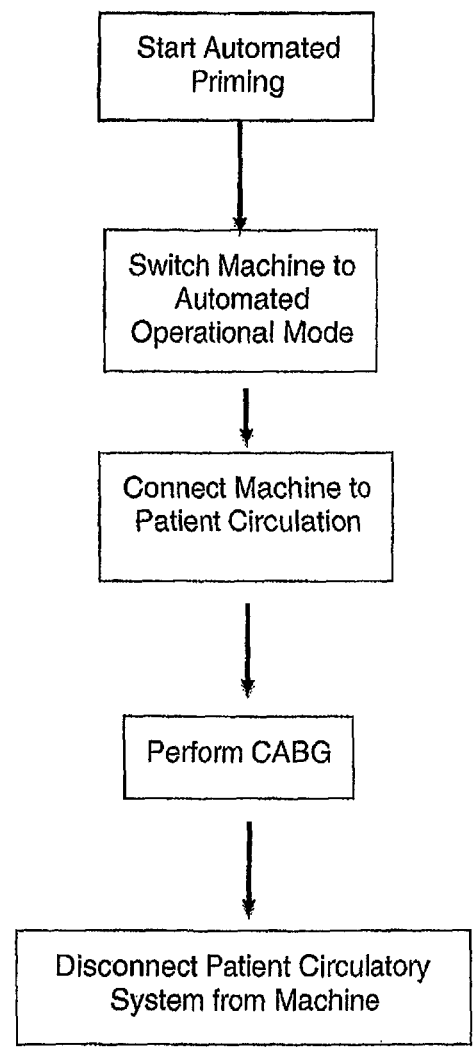
FIG. 21 is a flow chart showing method steps exemplary of the present methods.

In the case of a coronary artery bypass graft a graft vessel, such as a segment of saphenous vein, an internal thoracic artery, or a radial artery is taken from the patient, a cannulae is sutured into the heart, and cardiopulmonary bypass using the heart-lung machine is initiated. The aorta is clamped and the heart is stopped and cooled to, for example, 29° C. One end of the graft vessel is sutured a coronary artery beyond a blockage to be bypassed. The heart is then restarted, the other end of the graft vessel is sutured to the aorta while the heart is beating, and the heart-lung machine is disconnected from the patient (FIG. 21).

The method may include the addition of drugs or other additives to the blood by way of the heart-lung machine. For example, an anticoagulant may be added to the blood to prevent clotting while the heart is stopped.

In the case of percutaneous angioplasty or stent placement, a balloon is inflated inside a coronary artery to widen the passage or to expand a stent that will widen the artery and support the artery in a more open configuration to improve blood flow therethrough. The heart may be, but is usually not stopped for percutaneous angioplasty or stent placement, but the expansion of the balloon catheter inside the artery may cause the artery to rupture and necessitate emergency heart surgery. The heart-lung machine may be used in the event of such a complication or other complications that require the heart to be stopped or slowed. The heart-lung machine may be, but need not be, primed as a precaution before a possible complication.

The description of the invention is merely exemplary in nature and, thus, variations that do not depart from the gist of the invention are intended to be within the scope of the invention. Apparatus and methods comprising combinations of two or more of the various aspects and/or embodiments described herein and other variations are not to be regarded as a departure from the spirit and scope of the invention.

What is claimed is:

1. A method for performance of a percutaneous angioplasty or stent placement procedure in a subject with concurrent cardiopulmonary support, said method comprising the steps of:
   a) obtaining an extracorporeal cardiopulmonary support device which comprises a venous blood inlet, a blood pump, a blood reservoir which receives blood from the venous blood inlet, an air extraction pump associated with the blood reservoir, a blood oxygenator which receives and oxygenates blood from the blood reservoir, an oxygenated blood outlet through which oxygenated blood flows from the blood oxygenator, a filter for filtering oxygenated blood flowing through the oxygenated blood outlet, a bubble detector for detecting the presence of bubbles in oxygenated blood flowing through the oxygenated blood outlet, a quick acting clamp located on the oxygenated blood outlet downstream of the bubble detector and control circuitry adapted to perform priming of the device, when initiated, in an automated manner without human intervention, and to thereafter control operation of the cardiopulmonary support device without the need for a perfusionist;

b) initiating the priming, thereby causing the device to become primed in said automated manner without human intervention;

c) positioning a venous cannula in a vein of the subject and an arterial cannula in an artery of the subject;

d) connecting the venous cannula to the venous blood inlet of the extracorporeal cardiopulmonary support device and connecting the arterial cannula to the oxygenated blood outlet of the extracorporeal cardiopulmonary support device;

e) positioning a balloon catheter having an inflatable balloon in the vasculature of the subject and inflating the balloon to effect an angioplasty or stent placement; and f) if, upon inflation of the balloon, a complication selected from rupture of a blood vessel, cardiopulmonary arrest or cardiopulmonary insufficiency occurs, causing the extracorporeal cardiopulmonary support device to operate, without a perfusionist, such that the blood pump pumps venous blood from the patient's venous vasculature, through the venous cannula, through the venous blood inlet, into the reservoir and from the reservoir to the oxygenator wherein the venous blood becomes oxygenated, and thereafter pumps the oxygenated blood from the oxygenator, through the oxygenated blood outlet, through the arterial cannula and into the patient's arterial vasculature;

wherein the priming is completed before the inflation of the balloon such that extracorporeal cardiopulmonary support device is primed and ready for use at the time the balloon is inflated.

2. A method according to claim 1 wherein the device further comprises a sensor for sensing collection of air in the reservoir and wherein, during Step f, the extracorporeal cardiopulmonary support device automatically causes the air extraction pump to extract air from the blood reservoir when a collection of air is sensed by the sensor.

3. A method according to claim 2 wherein said blood reservoir is separated into a lower blood-containing space and an upper air-containing space by a membrane that is permeable to blood but not to air bubbles and wherein the sensor for sensing when air collects in the blood reservoir senses when a quantity of air has collected on one side of the membrane.

4. A method according to claim 1 wherein the extracorporeal cardiopulmonary support device further comprises a recirculation conduit connecting the blood reservoir to the oxygenated blood outlet, upstream of the quick acting clamp, and a recirculation conduit clamp for closing the recirculation conduit;

wherein, during Step e, the extracorporeal cardiopulmonary support device automatically causes the quick action clamp to close and the recirculation conduit clamp to open when the bubble detector detects a bubble, thereby causing oxygenated blood and the sensed air bubble to recirculate from the oxygenated blood outlet and into the blood reservoir where the air bubble is separated from the blood.

5. A method according to claim 1 wherein the extracorporeal cardiopulmonary support device further comprises a first pressure sensor for sensing the pressure of venous blood upstream of the oxygenator, a second pressure sensor for sensing the pressure of oxygenated blood downstream of the oxygenator.

6. A method according to claim 1 wherein perforation of a blood vessel occurs during performance of the angioplasty or stent placement and Step e is carried out for a time period sufficient to allow emergency surgery to be performed to repair the perforated blood vessel.

7. A method according to claim 1 wherein the heart becomes stopped or slowed resulting in cardiopulmonary arrest or insufficiency during performance of the angioplasty or stent placement and Step e is carried out until sufficient cardiopulmonary function is restored.

* * * * *